United States Patent

Neame

[11] Patent Number: 5,881,726
[45] Date of Patent: Mar. 16, 1999

[54] LARYNGEAL MASK AIRWAYS AND THEIR MANUFACTURE

[75] Inventor: Simon Neame, Broadstairs, England

[73] Assignee: Smiths Industries Public Limited Company, London, England

[21] Appl. No.: 961,038

[22] Filed: Oct. 30, 1997

[30] Foreign Application Priority Data

Nov. 19, 1996 [GB] United Kingdom .................... 9624029

[51] Int. Cl.$^6$ .................................................. A61M 16/00
[52] U.S. Cl. .................. 128/207.15; 128/207.14
[58] Field of Search ........................ 128/207.15, 207.14, 128/206.26, 207.16, 200.26; 152/565; 604/96, 97, 174; 156/304.1

[56] References Cited

U.S. PATENT DOCUMENTS

| | | | |
|---|---|---|---|
| 2,792,837 | 5/1957 | Kardos | 128/351 |
| 2,804,123 | 8/1957 | Kling | 155/69 |
| 4,210,478 | 7/1980 | Shoney | 156/242 |
| 4,509,514 | 4/1985 | Brain . | |
| 5,303,697 | 4/1994 | Brain . | |
| 5,305,743 | 4/1994 | Brain . | |
| 5,391,248 | 2/1995 | Brain . | |

FOREIGN PATENT DOCUMENTS

| | | |
|---|---|---|
| 0389272 | 9/1990 | European Pat. Off. . |
| 0448878A2 | 10/1991 | European Pat. Off. . |
| 2205499 | 12/1988 | United Kingdom . |
| WO/97/12640 | 4/1997 | WIPO . |

*Primary Examiner*—John G. Weiss
*Assistant Examiner*—Charles W. Anderson
*Attorney, Agent, or Firm*—Pollock, Vande Sande & Amernick

[57] ABSTRACT

The mask at the end of a laryngeal mask assembly is made from a flexible cylindrical member having radially projecting ledges at each end. The ends of the cylindrical member are folded axially within the member to form an annulus with an inner rib formed by the contacting ledges. One side of the rib is located in a channel around an elliptical mount member at the patient end of a tube. The other side of the rib is located in a channel around a plate, which is attached to the mount member trapping the rib between the plate and the mount member so that a cuff is formed extending around the mount member.

8 Claims, 3 Drawing Sheets

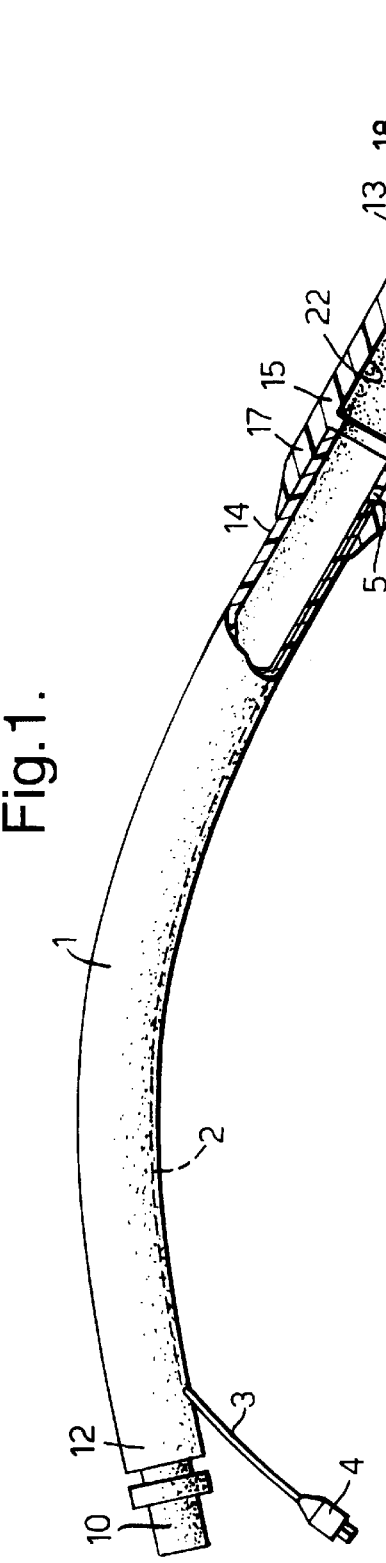
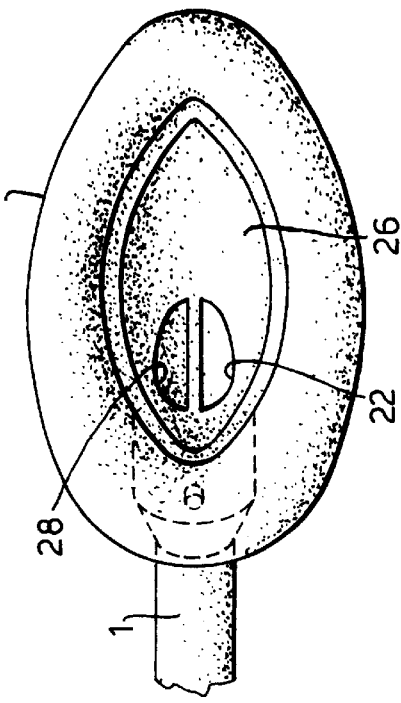
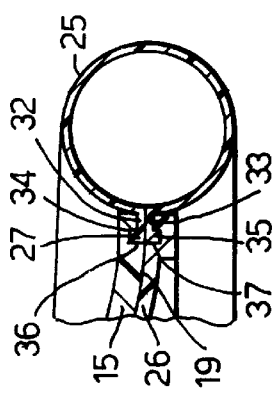

LARYNGEAL MASK AIRWAYS AND THEIR MANUFACTURE

CROSS REFERENCE TO RELATED APPLICATIONS

The subject matter of the present invention is related to the inventions described in Neame et al., U.S. application Ser. No. 08/925,668, filed Sep. 9, 1997 now pending for "Laryngeal Mask Airways and their Manufacture", and Neame et al., U.S. application Ser. No. 08/956,358, filed Oct. 23, 1997 now pending for "Laryngeal Mask Airways and their Manufacture".

BACKGROUND OF THE INVENTION

This invention relates to laryngeal mask airways and their manufacture.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5355879, U.S. Pat. No. 5305743, U.S. Pat. No. 5297547, U.S. Pat. No. 5282464, GB 2267034, U.S. Pat. No. 5249571, U.S. Pat. No. 5241956, U.S. Pat. No. 5303697, GB 2249959, GB 2111394, EP 448878, U.S. Pat. No. 4995388, GB 2205499, GB 2128561 and GB2298797.

Laryngeal masks have several advantages over endotracheal tubes, which are longer and seal with the trachea below the vocal folds. It can be difficult, however, to manufacture the patient end of the mask at low cost.

BRIEF SUMMARY OF THE INVENTION

It is an object of the present invention to provide an improved laryngeal mask assembly and method of manufacture.

According to one aspect of the present invention there is provided a method of manufacture of a laryngeal mask assembly including the steps of providing an elongate tube having a mount member at the patient end of the tube, the mount member being generally elliptical and the tube opening at the patient end of the assembly via an opening on the forward surface of the mount member, providing a cylindrical member of a flexible material, folding opposite ends of the cylindrical member axially of the cylinder towards one another to form an annulus, and attaching the annulus to the mount member to form an annular cuff surrounding the mount member at the patient end.

The cylindrical member may have a waisted portion projecting inwardly. The cylindrical member preferably has a radially-projecting ledge at each end, the ledges being brought together by the step of folding the ends of the cylinder towards one another. A part of one of the ledges is preferably located in a recess in the mount member. The ledges may be interlocked with one another. A plate may be secured with the mount member extending over a part of the annulus, so as to attach the annulus to the mount member. The plate preferably has a recess, a part of the ledges at opposite ends of the cylindrical member being located in respective recesses in the mount member and in the plate. The mount member and the plate preferably have a concave surface forming a recess at the patient end of the assembly.

According to another aspect of the present invention there is provided a laryngeal mask assembly made by the above one aspect of the invention.

A laryngeal mask airway assembly and its method of manufacture, according to the present invention, will now be described, by way of example, with reference to the accompanying drawings.

BRIEF DESCRIPTION OF THE DRAWINGS

FIG. 1 is a partly-sectional side elevation view of the assembly;

FIG. 2 shows a part of the patient end of the assembly to an enlarged scale;

FIG. 3 is an underside view of the patient end of the assembly;

DETAILED DESCRIPTION OF THE PREFERRED EMBODIMENTS

Figure 4:
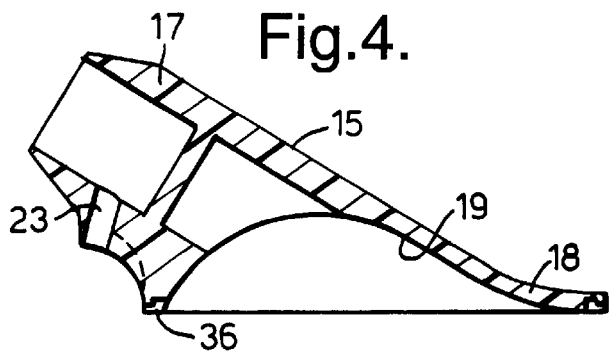
FIG. 4 is a sectional side elevation view of a mount member of the assembly.

With reference to FIGS. 1 to 4 and 7, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13, through a hole or slot 5 formed in the outside of the tube 1.

The mask portion 13 includes a mount member 15 moulded from a relatively stiff plastics material, such as PVC. The mount member 15 has a hollow cylindrical sleeve 17 at its rear end, in which the forward, patient end 14 of the tube 1 is inserted and joined. The forward, patient end 18 of the mount member 15 is of an inverted dish shape with a generally elliptical or egg-shape outline and with a concave recess 19. A bore 22 extends forwardly through the mount member 15, as a continuation of the bore through the sleeve 17, and opens into the rear part of the recess 19. The hole 5 opening from the inflation lumen 2 communicates with a side passage 23 in the mount member 15.

The mask portion 13 also includes an inflatable annular cuff 25 secured to the mount member 15 by means of a mounting plate 26. The plate 26 has the same shape as the recess 19 in the mount member 15 and traps a rib 27 around the inside circumference of the cuff 25 between the plate and the mount member 15. The plate 26 has an aperture 28 aligned with the bore 22 and which may have a series of holes or slits to prevent entry of the epiglottis into the bore 22 during insertion of the mask assembly. A spigot 29 on the upper surface of the cuff 25 is bonded into the side passage 23 through the mount member 15 so that the inside of the cuff communicates with the inflation lumen 2.

Figure 5:
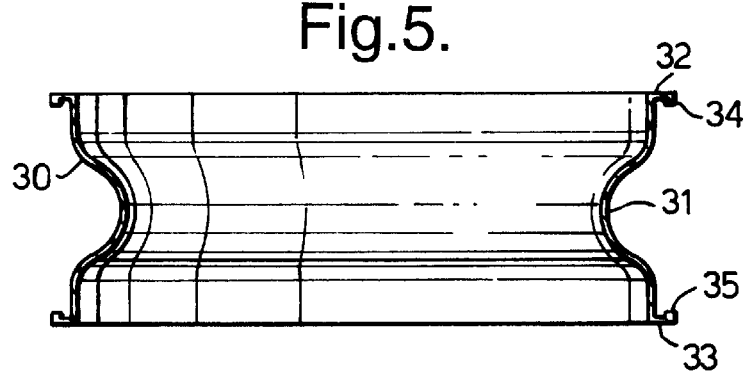
FIG. 5 is a sectional side elevation of a part of the assembly at a preliminary stage of manufacture.
Figure 6:
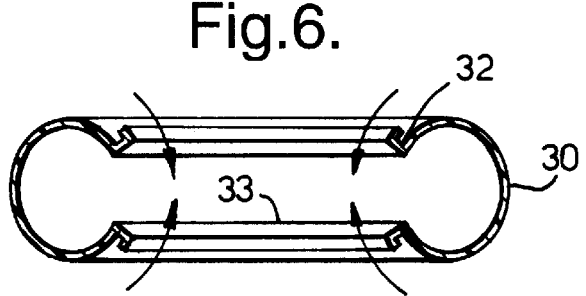
FIG. 6 shows a later stage of manufacture of the part shown in FIG. 5.
Figure 7:
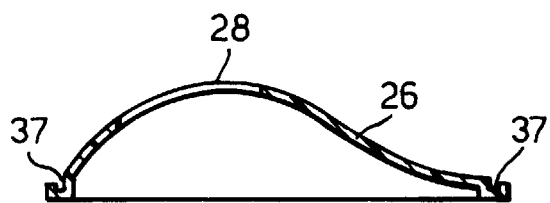
FIG. 7 is a sectional side elevation view of another part used in manufacture of the assembly.

With reference now to FIGS. 5 and 6, the inflatable cuff 25 is made by first moulding a generally cylindrical member 30 from a flexible plastics material, such as PVC, polyurethane, silicone, EVA, TPE, polyether block amide or the like. The cylindrical member 30 has a waisted portion 31 of semi-circular shape extending around the member midway along its length, the waisted portion projecting inwardly of the member. At each opposite end, the cylindrical member 30 has a radially-projecting ledge 32 and 33, each having an enlarged bead 34 and 35 of square shape projecting from the facing surfaces of the two ledges.

The next step, as shown in FIG. 6, is to fold the opposite ends of the cylinder 30 inwardly towards one another along the axis of the cylinder so that the flat surfaces of the two ledges 32 and 33, that is, the surfaces opposite those from which the beads 34 and 35 project, come together and contact one another. The contacting surfaces of the ledges 32 and 33 are coated with a solvent or adhesive so that they bond together to form the rib 27 and to form the cylindrical member 30 into the annular cuff 25, which has substantially the same diameter as the cylindrical member. The spigot 29 is then bonded to a hole in the upper surface of the cuff, which may be formed before or after joining the two ledges 32 and 33 together. The spigot 29 could instead be joined to the cylinder 30 before folding its ends in together. Alternatively, the spigot could be moulded integrally with the cylinder 30. The location of the hole and spigot 29 is selected to align with the side passage 23 in the mount member 15. The cuff 25 is then positioned against the lower surface of the mount member 15, so that the spigot 29 aligns with the side passage 23 and so that the upwardly-projecting bead 34 around the ledge 32 locates in a recess or channel 36 formed around the lower surface of the mount member 15. A solvent or adhesive is applied to the spigot 29 and to the bead 34 or channel 36 to bond the cuff 25 to the mount member 15 and to seal the spigot in the side passage 23. The mounting plate 26 (shown most clearly in FIG. 7) is then applied over the rib 27 of the cuff 25, the plate having a peripheral recess or channel 37 on its upper surface in which the downwardly-projecting bead 35 is located, the plate being bonded to the concave recess 19 of the mount member 15 by means of a solvent or adhesive.

Figure 8:
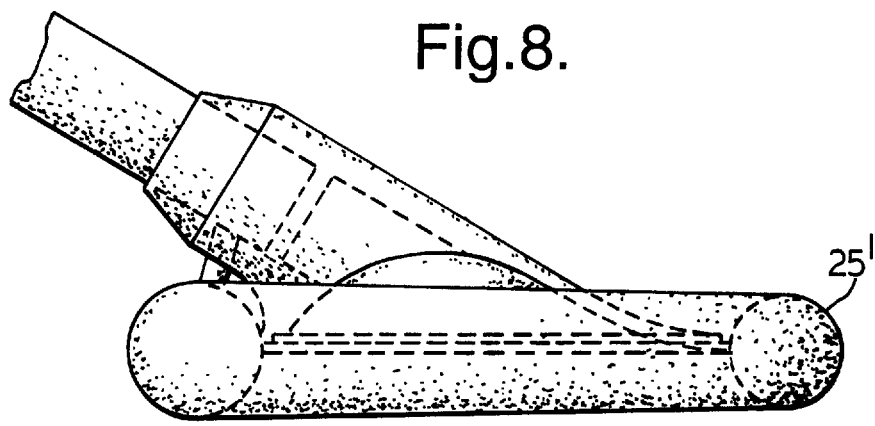
FIG. 8 is a side elevation view of an alternative assembly.
Figure 9:
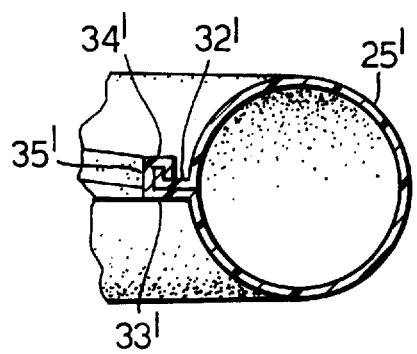
FIG. 9 shows a part of FIG. 8 to an enlarged scale.
Figure 10:
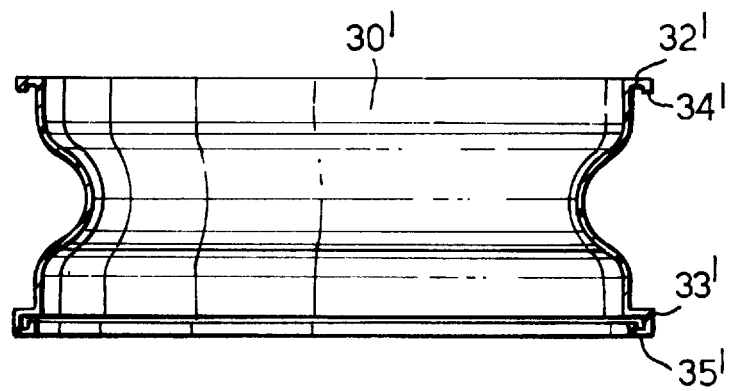
FIG. 10 shows a part of the alternative assembly at a preliminary stage in manufacture.

It is not essential for the assembly to have a mounting plate. For example, as shown in FIGS. 8 to 10, the ledges 32' and 33' of the cuff 25' could be formed so that they interlock when the ends of the cylindrical member 30' are folded in. The two ledges 32' and 33' both project downwardly when the cylindrical member 30' is in its natural shape (FIG. 10), one ledge 32' being similar to the ledges 32 and 33 of the cylindrical member 30 described above, the other ledge 33' having a rim 35' with a hook-shape section. When the ends of the cylindrical member 30' are bent inwardly together, as shown most clearly in FIG. 9, the two rims projects upwardly so that one rim 35' can be hooked over the other 34' and mechanically retain the two ends together against the resilience of the material of the cylindrical member. Because this overcomes the force tending to separate the two ledges, the cuff can be secured to the lower surface of the mounting member without any need for the mounting plate.

The airway can be easily manufactured in this way at low cost.

What I claim is:

1. A method of manufacture of a laryngeal mask assembly comprising the steps of:

providing an elongate tube having a mount member at the patient end of the tube, said mount member being generally elliptical and said tube opening at the patient end of the assembly via an opening on a forward surface of said mount member; providing a cylindrical member of a flexible material; folding opposite ends of said cylindrical member axially of said member towards one another to form an annulus; and attaching said annulus to said mount member to form an annular cuff surrounding said mount member at the patient end.

2. A method according to claim 1, wherein said cylindrical member has a waisted portion projecting inwardly.

3. A method according to claim 1, wherein said cylindrical member has a radially-projecting ledge at each end, and wherein the said ledges are brought together by said step of folding the ends of said cylinder towards one another.

4. A method according to claim 3, wherein a part of one of said ledges is located in a recess in said mount member.

5. A method according to claim 3, wherein said ledges are interlocked with one another.

6. A method according to claim 1, wherein a plate is secured with said mount member extending over a part of said annulus so as to attach said annulus to said mount member.

7. A method of manufacture of a laryngeal mask assembly comprising the steps of:

providing an elongate tube having a mount member at the patient end of the tube, said mount member being generally elliptical and said tube opening at the patient end of the assembly via an opening on a forward surface of said mount member; providing a cylindrical member of a flexible material, said cylindrical member having a radially-projecting flange at each end; folding opposite ends of said cylindrical member axially of said member towards one another to form an annulus with said flanges contacting one another; placing said annulus against said mount member; and securing a plate member on said mount member to trap said flanges between said plate member and said mount member, so as to form an annular cuff surrounding said mount member at the patient end.

8. A method of manufacture of a laryngeal mask assembly comprising the steps of:

providing an elongate tube having a mount member at the patient end of the tube, said mount member being generally elliptical, said mount member having a channel extending around its forward surface, and said tube opening at the patient end of the assembly via an opening on a forward surface of said mount member; providing a cylindrical member of a flexible material, said cylindrical member having a radially-projecting flange at each end; folding opposite ends of said cylindrical member axially of said member towards one another to form an annulus with said flanges interlocking with one another; and securing said interlocked flanges in said channel around said mount member, so as to form an annular cuff surrounding said mount member at the patient end of the assembly.

* * * * *